(12) United States Patent
Veltri

(10) Patent No.: US 8,449,685 B2
(45) Date of Patent: May 28, 2013

(54) AUTOMATIC SANITATION SYSTEM

(76) Inventor: Joseph Anthony Veltri, East Dundee, IL (US)

(*) Notice: Subject to any disclaimer, the term of this patent is extended or adjusted under 35 U.S.C. 154(b) by 418 days.

(21) Appl. No.: 12/777,050

(22) Filed: May 10, 2010

(65) Prior Publication Data

US 2010/0282279 A1 Nov. 11, 2010

Related U.S. Application Data

(60) Provisional application No. 61/177,251, filed on May 11, 2009.

(51) Int. Cl.
*B08B 3/02* (2006.01)
*B08B 9/00* (2006.01)

(52) U.S. Cl.
USPC ...... 134/18; 134/22.1; 134/22.16; 134/22.17; 134/26; 134/34

(58) Field of Classification Search
USPC ............... 4/574.1, 621, 622, 625, 650, 653
See application file for complete search history.

(56) References Cited

U.S. PATENT DOCUMENTS

| | | | | |
|---|---|---|---|---|
| 5,960,483 A | * | 10/1999 | Delzer et al. | 4/420 |
| 2005/0081292 A1 | * | 4/2005 | Lev et al. | 4/622 |
| 2006/0207017 A1 | * | 9/2006 | Lev et al. | 4/622 |

* cited by examiner

*Primary Examiner* — Saeed T Chaudhry
(74) *Attorney, Agent, or Firm* — The Gray Law Group, Ltd.; Steven L. Fisher-Stawinski

(57) ABSTRACT

A cover for a pedicure spa containing an automatic sanitation apparatus is disclosed. When activated, the cover automatically sprays disinfectant in a circular motion from a nozzle on the bottom of the cover. The interior surfaces of the pedicure basin are treated with the disinfectant solution. The pedicure basin is thereby efficiently and thoroughly sanitized.

3 Claims, 3 Drawing Sheets

AUTOMATIC SANITATION SYSTEM

CROSS-REFERENCE TO RELATED PATENT APPLICATIONS

This application claims priority from U.S. Provisional Application Ser. No. 61/177,251, filed May 11, 2009 and titled "Automatic Sanitation System," which is incorporated herein by reference in its entirety.

BACKGROUND

Spas are well known for use in facilitating comfort and relaxation. Pedicure spas specifically allow for treatment and comfort of the feet of a person in addition to receiving other incorporated services. Spa basins must be thoroughly cleaned after every use to eliminate bacteria build up. The construction of a pedicure spa requires that a spa professional complete a pedicure and allow a client to leave before cleaning the basin of the spa. The client typically receives a pedicure at the pedicure spa and then moves to a different station for another service. The present invention provides an apparatus and method for automatically cleaning a pedicure spa between users.

SUMMARY

One embodiment on the invention relates to an apparatus for sanitizing a foot basin, comprising a cover adapted to engage a pedicure foot basin, a liquid reservoir, a nozzle assembly disposed on the bottom surface of the cover and connectively coupled to the first liquid reservoir, a controller, and an activation button.

Another embodiment of the present invention relates to a method for sanitizing a foot basin. The method comprises the steps of providing pedicure basin having an interior surface and an open top end, draining the foot basin upon completion of a first user's pedicure bath, providing a first liquid reservoir containing a first disinfectant solution, and providing a cover having a nozzle assembly connectively coupled to the liquid reservoir, engaging the cover to the open top end of the pedicure basin, pressing an activation button to initiate a cleaning routine, thereby causing the nozzle assembly to spray an interior surface of the foot basin, and disengaging the cover prior to a second user's pedicure bath.

How these and other advantages and features of the present invention are accomplished (individually, collectively, or in various subcombinations) will be described in the following detailed description of the preferred and other exemplary embodiments, taken in conjunction with the FIGURES.

DETAILED DESCRIPTION

Figure 1:
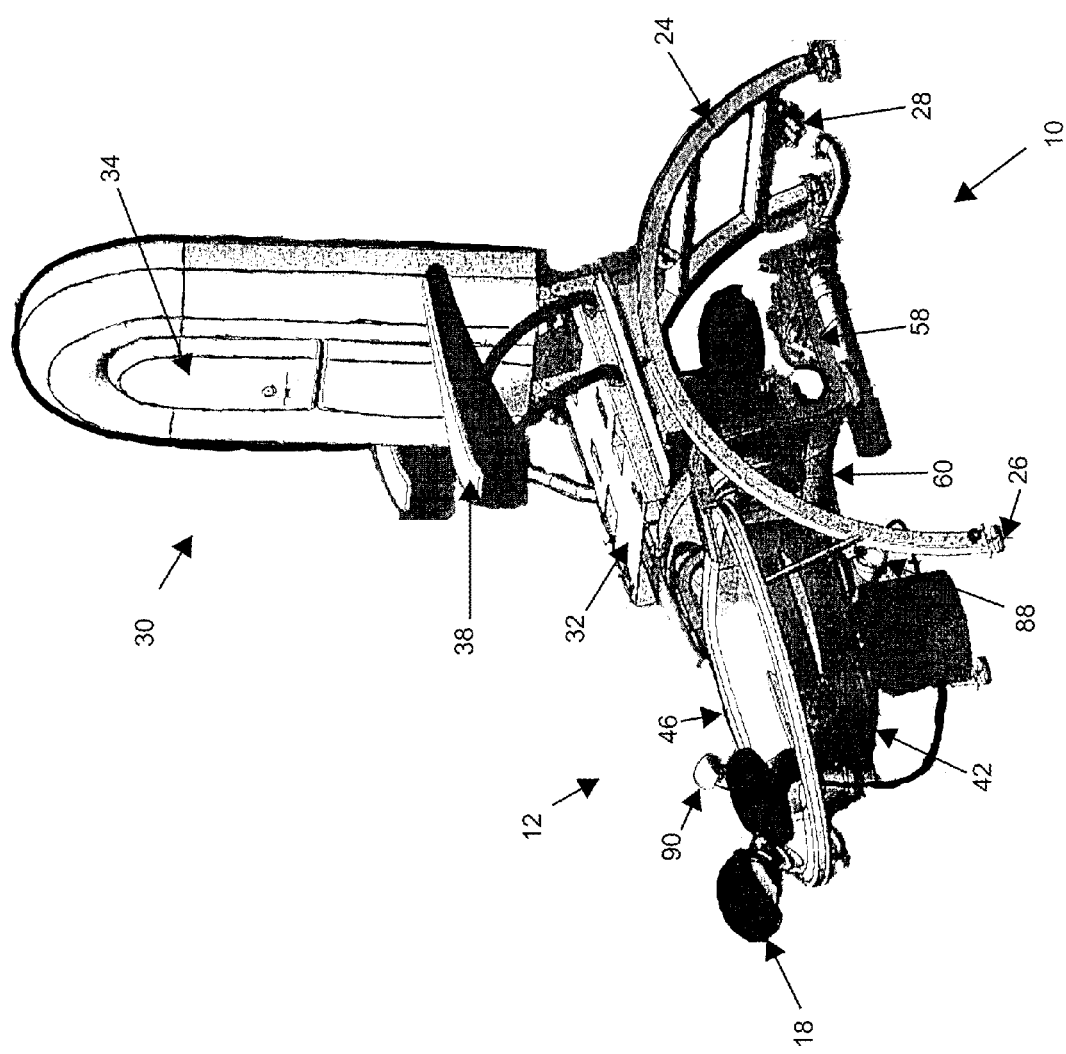
FIG. 1 is a perspective drawing of a pedicure spa having a cover comprising an automatic sanitation apparatus, with the cover retracted.

Referring generally to the FIGURES, spa 10 is intended to seat a person in order to facilitate administering services to that person. For example, a person may receive services such as a pedicure, manicure or haircut while sitting in the seat. Spa 10 generally includes a base portion 12 and a seat 30. Base portion 12 supports and houses the individual components of the spa apparatus. Base portion 12 generally has a front end 16 and a rear end 17. Base portion 12 may be formed of metal, plastic, fiberglass, ceramic, glass, or a combination of any of these materials.

Base portion 12 is intended to be stationary, and is typically placed in a position where it can be connected to the plumbing and electrical components of a building. Referring to FIG. 1, base portion 12 generally includes a supporting frame 20, one or more base shroud panels, a foot basin 40, one or more plumbing and drain components, one or more faucets, and a cover 60.

Supporting frame 20 structurally supports seat 30, foot basin 40, and cover 60. In one embodiment, supporting frame 20 is a rigid metal frame comprising side arch members 24 and transverse members 28. Side arch members 24 provide support for foot basin 40, seat 30, and the weight of a person sitting thereon. In various example embodiments, supporting frame 20 may be composed of any metal (e.g. steel, iron, aluminum, titanium), plastic, fiberglass, or any other suitable material or combination thereof. Alternatively, supporting frame 20 may be integrally formed into base portion 12, without a separate internal frame.

Each bottom end of side arch members 24 may be provided with a foot pad 26, thereby reducing the risk of damage to floor surfaces and preventing base portion 12 from sliding during use. Foot pads 26 may be adjustable in order to vary the height of base portion 12, or to level base portion 12 of spa 10 if it is resting on an uneven surface. In one embodiment, foot pads 26 may be composed of a polymer (e.g., plastic, rubber) disc, or composed of another material. In another embodiment, one or more foot pads 26 may be wheels or casters that facilitate the movement of base portion 12.

Referring to FIG. 1, foot basin 40 is a concave, liquid-retaining basin defined by a generally horizontal bottom wall 42, a generally vertical peripheral wall 44, and an open top end 46. Foot basin 40 is sized to enable a user to accommodate both feet in the basin while receiving a foot soak and air bubble massage. During operation, the interior of foot basin 40 is filled with and retains a liquid pedicure solution. The pedicure solution may be water alone, water combined with soaps, oils, surfactants, salts, or other materials, or another liquid composition. The foot basin may be pipe-free, substantially free of obstructions, or both. In other embodiments, the foot basin may include propellers, impellors, or pump-driven water jets to provide the user with a pleasing foot massage.

As used herein, the term "pipe-free" refers to a foot basin that is substantially free of fluid piping other than one or more fresh water faucets and a drainage connection. By reducing or eliminating water piping within the spa system, a corresponding reduction in difficult-to-clean cavities and void spaces is achieved.

As used herein, the term "substantially free of obstructions" refers to a foot basin that is substantially free of internal obstacles such as propellers or impellors used to effect water movement, thereby reducing or eliminating the presence of difficult-to-clean cavities and void spaces.

Peripheral wall 44 may be circular, ellipsoid, or any other shaped sized to fit the user's feet. In a preferred embodiment, peripheral wall 44 is generally smooth to facilitate effective cleaning and sanitation. Similarly, the transition between peripheral wall 44 and bottom wall 42 is also generally smooth to minimize areas where bacteria may be concealed and promote effective sanitation. The bottom wall 42 of foot basin 40 may be further provided with a pair of surface features contoured to provide complimentary support to the foot arches of the user. Surface features may be either a contoured depression in bottom wall 42, or a foot support raised above bottom wall 42. The bottom wall 42 and peripheral wall 44, and any surface features inside the foot basin, together comprise the interior surfaces of the foot basin.

Foot basin 40 may be formed from an acrylonitrile-butadiene-styrene (ABS) backing or interior. In other embodiments, foot basin 40 may be formed from another plastic, fiberglass, metal, ceramic, glass, or a combination of any of these materials. Foot basin 40 may be integrally molded into base portion 12, or may be separately formed and affixed to supporting frame 20.

Figure 2:
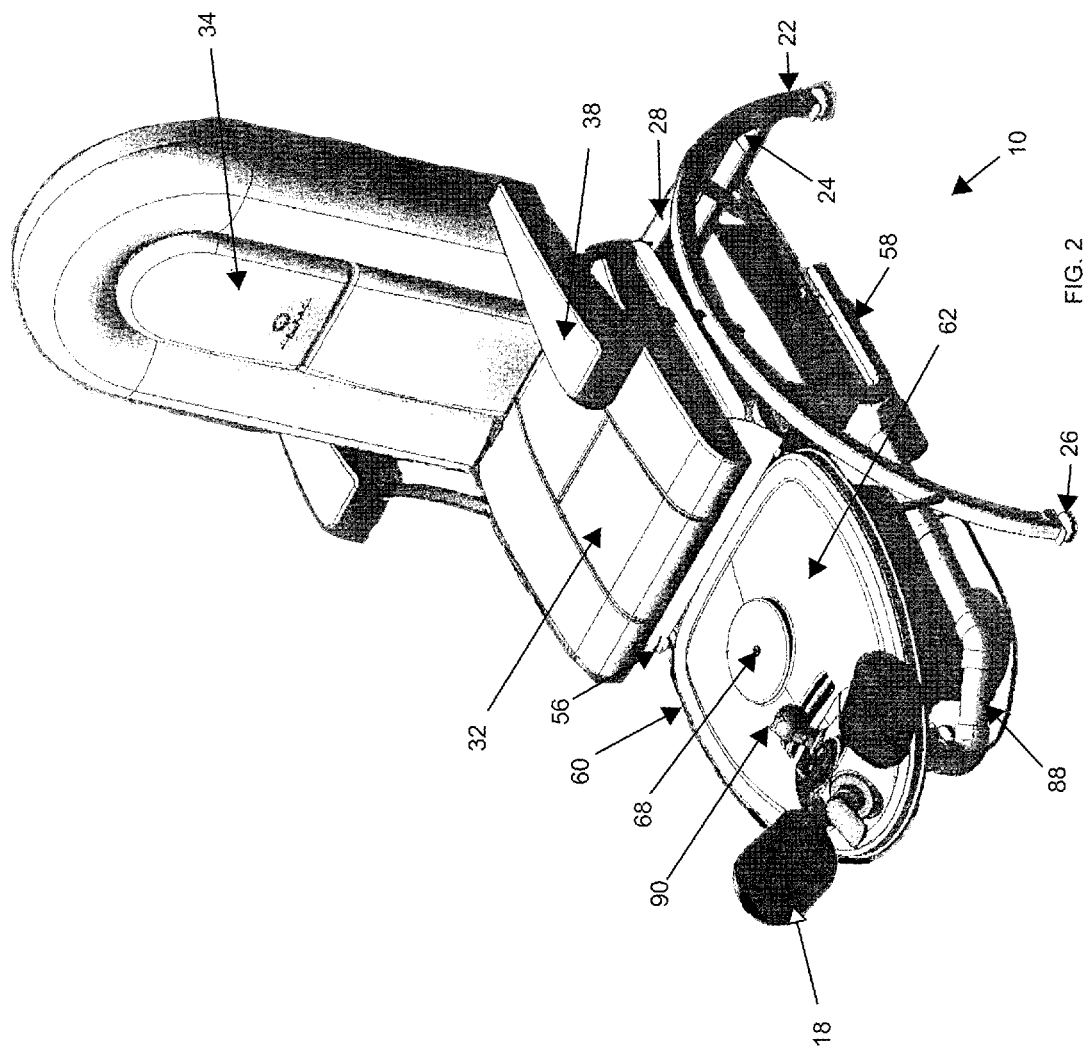
FIG. 2 is a perspective drawing of a pedicure spa, with the cover positioned atop a foot basin.

Referring to FIGS. 1 and 2, cover 60 is adapted to removably engage with the open top end 46 of foot basin 40. Cover 60 may cover a portion, substantially all, or the entire open top end 46 of foot basin 40. Cover 60 is generally planar, having a top surface 62 and a bottom surface 63, and a left edge 64 and a right edge 65. Cover 60 is provided with a nozzle assembly 70 disposed on bottom surface 63. Cover 60 may also be provided with a seal or gasket to prevent the escape of water or any other liquid from the foot basin 40. Cover 60 may also be provided with an activation button 68 disposed on top surface 62, or, alternatively, anywhere on spa 10. In other embodiments, activation button 68 may be replaced by a remote wired or wireless activation signal.

In one embodiment, cover 60 is formed from an acrylonitrile-butadiene-styrene (ABS) material. In other embodiments, cover 60 may be formed from another plastic, fiberglass, metal, ceramic, glass, or a combination of any of these materials. In another embodiment, cover 60 may include one or more areas of increased flexibility to allow the cover to negotiate bends in slide rails 58. In other embodiments, cover 60 may be formed of a flexible material such as rubber or a soft plastic.

In one embodiment, supporting frame 20 is provided with slide rails 58 adapted to receive the left edge 64 and right edge 65 of cover 60. Left edge 64 and right edge 65 may optionally be provided with a low-friction material, guide wheels, or guide pins to slideably engage slide rails 58. Slide rails 58 may be a linear track permitting cover 60 to be retracted towards the rear end 17 of base portion 12. In other embodiments, slide rails 58 may be arcuate, or another shape. Cover 60 may thereby be slideably retracted to the rear of base unit 12 while the foot basin is in use.

In another embodiment, cover 60 may be hingedly attached to base portion 12 or foot basin 40, thereby permitting the cover to be rotated away from foot basin 40. A hinge may be disposed along an edge of cover 60 and substantially parallel to the top and bottom surfaces of cover 60. Alternatively, the hinge may be a pin that is substantially perpendicular to the top and bottom surfaces of cover 60, thereby permitting rotational refraction in a plane substantially parallel to the cover. In yet another embodiment, cover 60 may be unattached to base portion 12, and stowed in a recess provided in base portion 12 when not in use. Embodiments where cover 60 is not affixed to base portion 12 may be provided with flexible electrical and liquid connections, or may be provided with quick-release connectors for electrical and liquid connections, or may not be provided with any electrical and fluid connections.

Figure 3:
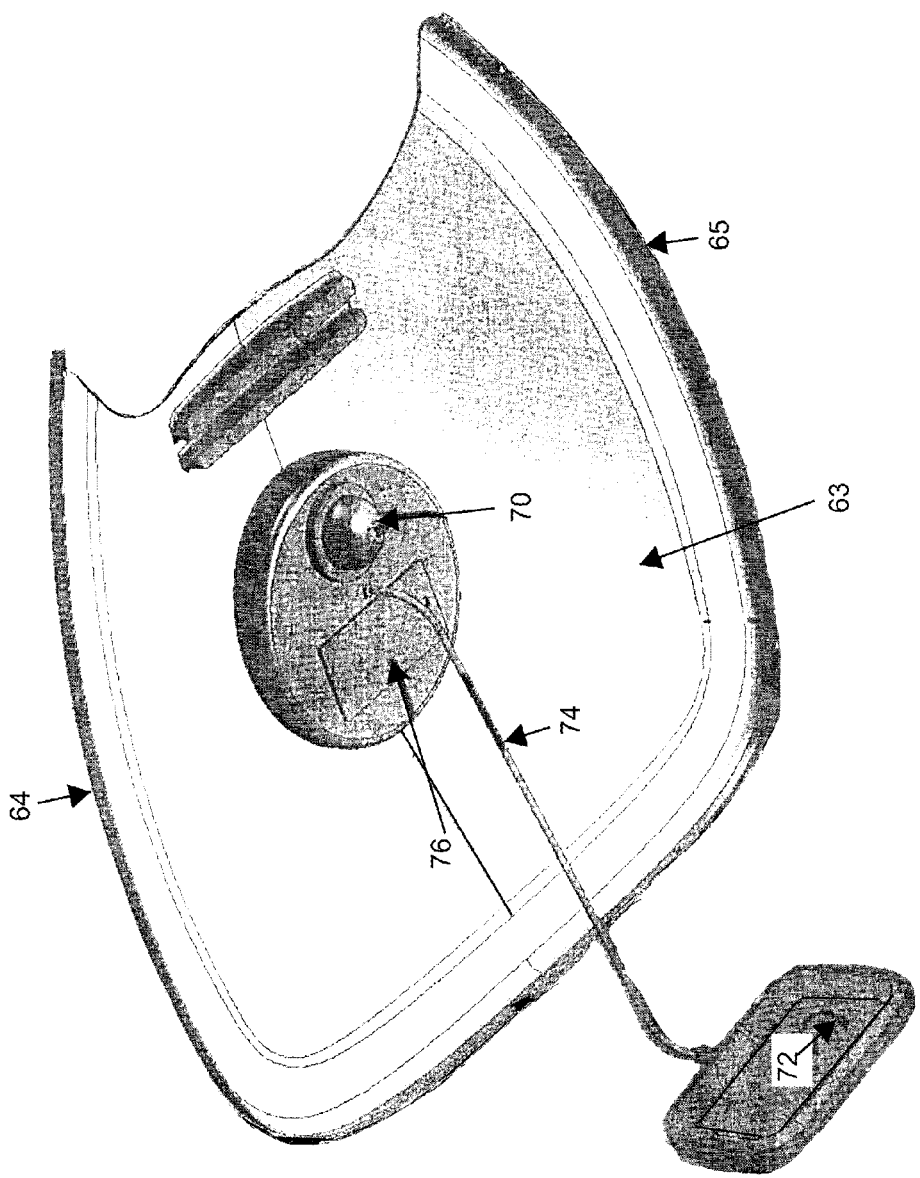
FIG. 3 is a perspective drawing of the underside of the cover.

Referring to FIG. 3, a liquid reservoir 72 may be disposed within cover 60 configured to store and dispense liquids. Alternatively, liquid reservoir 72 may be disposed within base portion 12. In other embodiments, liquid reservoir 72 may be located externally to spa 10. Spa 10 may also be provided with additional liquid reservoirs as necessary to contain different liquids, such as one or more surfactants, rinse solutions, and disinfectant solutions.

A nozzle assembly 70 is disposed on the bottom surface 63 of cover 60. Nozzle assembly 70 may be directly coupled to liquid reservoir 72, or a liquid line 74 may communicatively couple nozzle assembly 70 to liquid reservoir 72. Additionally, nozzle assembly 70 may be communicatively coupled to additional liquid reservoirs, or to plumbing connections, e.g., a cold water line, a hot water line, or a constant temperature water line. An electric motor may be used to rotate the nozzle assembly in a plane substantially parallel to bottom surface 63 of cover 60. Operation of nozzle assembly 70 is generally controlled by a controller 76.

In one embodiment, nozzle assembly 70 contains a single spray orifice shaped to deliver a fan of liquid to the interior surfaces of the foot basin. Liquid dispensed in a fan may be oriented vertically, horizontally, or in another orientation. In other embodiments, a single orifice may deliver a linear stream, a spray, or an atomized mist of liquid to the interior surfaces of the foot basin. Nozzle assembly 70 may be rotated while dispensing a liquid, thereby delivering the liquid to substantially all the interior surfaces of foot basin 40 in one revolution of nozzle assembly 70. In some embodiments, nozzle assembly 70 may deliver liquid directly to only a portion of the interior surfaces of foot basin 40.

In another embodiment, nozzle assembly 70 may be provided with a plurality of individual orifices to simultaneously spray multiple locations on the interior surfaces of foot basin 40. In some embodiments, nozzle assembly 70 may be configured to spray substantially all the interior surfaces of foot basin 40 simultaneously. In other embodiments, nozzle assembly 70 may include a plurality of orifices spaced apart at regular intervals, thereby delivering disinfectant to substantially all the interior surfaces of foot basin 40 in less than one full revolution of nozzle assembly 70. Nozzle assembly 70 may also be configured to deliver a high-pressure stream of liquid to provide a mechanical cleaning action to some or all the interior surfaces of foot basin 40.

In one embodiment, the automatic operation of the sanitation system is controlled by a controller 76. Controller 76 may be a microprocessor controller as is known in the art. Such a microprocessor controller may be located within cover 60 or elsewhere within base portion 12. Pressing activation button 68 generates an activation signal. The microprocessor controller may commence a cleaning routine when an activation signal is received and cover 60 is engaged to foot basin 40. The controller may also activate a visual or audio signal upon completion of a cleaning routine, such as a light, bell, whistle, or beep.

A cleaning routine may be composed of one or more cycles. A microprocessor controller may be programmed to direct nozzle assembly 70 to deliver a surfactant solution to the foot basin, deliver a disinfectant spray to the foot basin, deliver a rinse solution to the foot basin, and control the duration and timing of surfactant, disinfectant, and rinse cycles, and the like. The microprocessor controller may also be programmed to store the number of times the cleaning routine has been activated, dates of use, and other relevant usage information. The microprocessor controller may be further programmed with a plurality of different cleaning routines in compliance with varying manufacturer guidelines, health board regulations, national requirements, and so forth.

A microprocessor controller may be further coupled to a user interface allowing an operator to select modes of operation, choose different cleaning routines, change the duration and quantity of disinfection and rinse cycles, and the like. A user interface may comprise a display screen, such as an LCD display, and one or more user input buttons or keys. Such a user interface may be disposed on the base portion 12, elsewhere on spa apparatus 10, or at another location.

In other embodiments, controller 76 may be an on/off timer activated by pressing activation button 68. When activation button 68 is pressed, nozzle assembly 70 rotates and sprays one or more solutions for a pre-determined interval. In another embodiment, activation button 68 is a mechanical pump which simultaneously sprays a liquid and causes nozzle assembly 70 to be rotated.

Referring to FIGS. 1 and 2, base portion 12 can be substantially enclosed by a plurality of base shroud panels defining an interior volume. Base shroud panels may provide an aesthetically pleasing design. The base shroud panels also protect the interior volume of base portion 12. In one embodiment, base shroud panels are removably coupled to base portion 12 to allow for quick removal and greater access to the interior of base portion 12 for tasks such as repairs, cleaning, or to change the color or style of the shrouds. In another embodiment, one or more base shroud panels are hingedly connected to base portion 12 to permit access to the interior volume of base portion 12. In other embodiments, one or more base shroud panels are permanently coupled to base portion 12. Base shroud panels may also be integrally formed as part of base portion 12. Base shroud panels may be composed of a plastic, fiberglass, metal, other suitable material, or any combination thereof.

A seat 30 is configured to be coupled to supporting frame 20 and to provide a comfortable surface and sitting position for a person receiving services on spa 10. Seat 30 generally includes a cushion 32, a seat back 34, a splash guard 36, and one or two arm rests 38. Seat 30 can be configured in any manner known in the art. Seat 30 can also include additional functions known in the art, such as heating and massage, reclining capabilities, integrated sound or entertainment systems, and the like.

Base portion 12 may be provided with one or more plumbing components and drain components 88. Plumbing components may include cold water line, hot water line, or constant temperature water line. Alternatively, base portion 12 may be provided with a constant-temperature mixing valve to prevent scalding a user's feet. Plumbing components may be connected to one or more external fresh water supplies with custom quick disconnect fittings, or any other plumbing connection methods known in the art.

Drain components 88 may include a drain pipe that fits snuggly into a drain cowling to allow for seal and flexibility, or can be connected with other methods known in the art. Drain components 88 may be connectively coupled to a sanitary sewer or other drainage line in any manner known in the art. Alternatively, drain components 88 may be coupled to a wastewater holding tank provided in base portion 12. Such a wastewater holding tank may be emptied or drained at operator-determined intervals.

Base portion 12 may be provided with one or more faucets 90. Faucets may be configured to fill foot basin 40 with fresh water or another pedicure solution. Faucets may include a pull-out spray faucet, a cold water faucet, a hot water faucet, or a constant temperature faucet. Faucets may be used to fill the foot basin, rinse off the user's feet at the completion of the foot soak, and/or clean the foot basin.

Base portion 12 may also include foot rests 18. Foot rests may be located on any upper edge of foot basin 40. Foot rests 18 can be adjustable to accommodate users of different sizes. Foot rests 18 may be made of any material such as plastic or metal and the top of foot rests 18 may be cushioned or substantially hard. Alternatively, base portion 12 and foot basin 40 can be void of foot rests 18.

It is also important to note that the construction and arrangement of the elements of the system as shown in the preferred and other exemplary embodiments is illustrative only. Although only a certain number of embodiments have been described in detail in this disclosure, those skilled in the art who review this disclosure will readily appreciate that many modifications are possible. Other substitutions, modifications, changes, and omissions may be made in the design and arrangement of the exemplary embodiments without departing from the scope of the invention.

What is claimed is:

1. A method for sanitizing a foot basin, comprising:
providing pedicure basin having an interior surface and an open top end;
draining the foot basin upon completion of a first user's pedicure bath;
providing a first liquid reservoir containing a first disinfectant solution;
providing a cover having a nozzle assembly connectively coupled to the liquid reservoir;
engaging the cover to the open top end of the pedicure basin;
pressing an activation button to initiate a cleaning routine, thereby causing the nozzle assembly to spray an interior surface of the foot basin with the first disinfectant solution; and
disengaging the cover prior to a second user's pedicure bath.

2. The method of claim 1, wherein the method further comprises providing a second liquid reservoir containing a second liquid solution.

3. The method of claim 2, wherein the method further comprises sliding the cover to engage the cover from the pedicure basin.

* * * * *